US010543117B2

United States Patent
Riedy et al.

(10) Patent No.: US 10,543,117 B2
(45) Date of Patent: Jan. 28, 2020

(54) DUET STENT DEPLOYMENT SYSTEM AND METHOD OF PERFORMING A TRANSJUGULAR INTRAHEPATIC PORTOSYSTEMIC SHUNTING PROCEDURE USING SAME

(71) Applicant: Cook Medical Technologies LLC, Bloomington, IN (US)

(72) Inventors: Kelley Jean Riedy, Aurora, OH (US); Elizabeth Anne Hudson, Round Rock, TX (US); Thomas Wayne McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 16/411,516

(22) Filed: May 14, 2019

(65) Prior Publication Data

US 2019/0274856 A1 Sep. 12, 2019

Related U.S. Application Data

(62) Division of application No. 14/969,073, filed on Dec. 15, 2015, now abandoned.

(Continued)

(51) Int. Cl.
*A61F 2/06* (2013.01)
*A61F 2/966* (2013.01)
*A61F 2/82* (2013.01)

(52) U.S. Cl.
CPC ........ *A61F 2/966* (2013.01); *A61F 2002/826* (2013.01); *A61F 2002/9665* (2013.01); *A61F 2250/0098* (2013.01)

(58) Field of Classification Search
CPC .............. A61F 2/966; A61F 2002/9665; A61F 2250/0098; A61F 2002/826
(Continued)

(56) References Cited

U.S. PATENT DOCUMENTS 5,662,675 A 9/1997 Polanskyj Stockert et al.
6,123,723 A * 9/2000 Konya ..................... A61F 2/07
606/108

(Continued)

FOREIGN PATENT DOCUMENTS

EP 1044663 A2 10/2000
WO 03049794 6/2003

(Continued)

OTHER PUBLICATIONS

European Patent Office, Office Action, Applicant, Cook Medical Technologies LLC, Application No. 16155532.1-1113, Jul. 23, 2018, pp. 1-5, Netherlands.

*Primary Examiner* — Amy R Weisberg
(74) *Attorney, Agent, or Firm* — Liell & McNeil

(57) ABSTRACT

A duet stent deployment system is used in a transjugular intrahepatic portosystemic shunt procedure. The device has a versatility of adjusting to a patient's anatomy in vivo. The system includes exactly two self expanding stents mounted on an inner catheter and covered by an outer sheath that is moved among a pre-deployment configuration, a first deployment configuration and a second deployment configuration to position the stents in an overlapping configuration from the portal vein, through a shunt and into the hepatic vein, and terminating at the junction with the vena cava.

10 Claims, 3 Drawing Sheets

Related U.S. Application Data

(60) Provisional application No. 62/118,564, filed on Feb. 20, 2015.

(58) Field of Classification Search
USPC .......................................................... 604/529
See application file for complete search history.

(56) References Cited

U.S. PATENT DOCUMENTS

| | | |
|---|---|---|
| 6,143,016 A | 11/2000 | Bleam et al. |
| 6,210,338 B1 | 4/2001 | Afremov et al. |
| 6,273,895 B1 | 8/2001 | Pinchuk et al. |
| 7,056,336 B2 | 6/2006 | Armstrong et al. |
| 7,147,655 B2 | 12/2006 | Chermoni |
| 7,175,651 B2 | 2/2007 | Kerr |
| 7,192,440 B2 | 3/2007 | Andreas et al. |
| 7,300,456 B2 | 11/2007 | Andreas et al. |
| 7,303,798 B2 | 12/2007 | Bavaro et al. |
| 7,905,913 B2 | 3/2011 | Chew et al. |
| 7,922,654 B2 | 4/2011 | Boutillette et al. |
| 8,157,851 B2 | 4/2012 | Andreas |
| 8,343,205 B2 | 1/2013 | Sugimoto et al. |
| 9,603,696 B2 | 3/2017 | Hartley |
| 2004/0064070 A1 | 4/2004 | Vardi et al. |
| 2004/0215331 A1 | 10/2004 | Chew et al. |
| 2006/0142836 A1 | 6/2006 | Hartley |
| 2007/0067013 A1 | 3/2007 | Karpiel |
| 2007/0179587 A1 | 8/2007 | Acosta et al. |
| 2007/0282421 A1 | 12/2007 | Parker et al. |
| 2008/0234795 A1 | 9/2008 | Snow |
| 2009/0138065 A1 | 5/2009 | Zhang et al. |
| 2009/0171427 A1 | 7/2009 | Melsheimer et al. |
| 2009/0319019 A1 | 12/2009 | Parker |
| 2010/0137966 A1 | 6/2010 | Magnuson |
| 2010/0318182 A1 | 12/2010 | Qanadli |
| 2011/0190865 A1 | 8/2011 | McHugo et al. |
| 2011/0301685 A1 | 12/2011 | Kao |
| 2011/0307049 A1 | 12/2011 | Kao |
| 2012/0035705 A1 | 2/2012 | Giasolli |
| 2012/0232528 A1 | 9/2012 | Eli et al. |

FOREIGN PATENT DOCUMENTS

| | | |
|---|---|---|
| WO | 2006026371 | 3/2006 |
| WO | 2007007560 | 1/2007 |
| WO | 2007124289 | 11/2007 |

\* cited by examiner

DUET STENT DEPLOYMENT SYSTEM AND METHOD OF PERFORMING A TRANSJUGULAR INTRAHEPATIC PORTOSYSTEMIC SHUNTING PROCEDURE USING SAME

TECHNICAL FIELD

The present disclosure relates generally to a duet stent deployment system that carries exactly two self expanding stents, and more particularly to a stent deployment system for transjugular intrahepatic portosystemic shunting procedures.

BACKGROUND

Transjugular intrahepatic portosystemic shunting (TIPS) is an artificial channel within the liver that establishes communication between the portal vein and the hepatic vein. TIPS is sometimes used to treat portal hypertension that is often due to liver cirrhosis, which frequently leads to intestinal bleeding, esophageal bleeding and the build up of fluids within the abdomen. The TIPS procedure works by gaining access to the liver via the jugular vein, and then moving through the vena cava to the hepatic vein. A needle is then used to create a point of access (shunt) from the hepatic vein through the liver tissue into the portal vein. A guide wire is introduced to maintain access, and then a balloon catheter is placed over the wire and into the liver tissue. The balloon is inflated in the shunt to create a conduit that will accommodate the forthcoming stent. The balloon is deflated and removed. A stent introducer is then inserted and the portal end of the stent is deployed. The rest of the stent is then released and the balloon is reinserted and reinflated to assure that the stent is fully patent. The stented shunt allows for pressure relief in the portal vein, and blood can return to mostly a normal path through the liver, and therefore reduce some of the symptoms described above.

There are a variety of problems associated with the current TIPS procedure. One problem is that the stent length and sometimes diameter needed for a patient is uncertain, even with careful measuring and estimation. Physicians would like to control the length and diameter of the stent during and post-procedure. For instance, due to substantial variations among patients' internal anatomy geometry, stent sizing can require that a hospital maintain a wide variety of stent introducers with stents of varying lengths to accommodate all potential patients. In addition, when it is necessary for the physician to complete the procedure with the implantation of two stents, the first stent introducer must be withdrawn and a second stent introducer must be brought into the patient, increasing costs, procedure times and complication risks to the patient. An additional problem is that this procedure is expensive due to physician operating time and materials. Lastly, a covered stent is often integral to the procedure, and physicians generally prefer longer sleeve covered stents. These covered stents have an outer coating that keeps bile out of the shunt, and may include an inner coating that promotes platelet growth and blood flow. European patent application EP 1044663A2 is of interest for teaching a sleeved intrahepatic endoprosthesis (stent) in which two members can be connected telescopically to adapt to the length of stenting required for a particular patient. However, this reference teaches mounting the two stent members on separate delivery devices requiring withdrawal of the first delivery device before the second stent can be implanted using a second delivery device.

The present disclosure is directly toward one or more of the problems set forth above.

SUMMARY OF THE DISCLOSURE

In one aspect, a duet stent deployment system includes exactly two stents mounted on a distal segment of an inner catheter. The two stents include a primary stent and a secondary stent. An outer sheath is slidably mounted on the inner catheter, and movable along an axis of the inner catheter from a pre-deployment configuration to a first deployment configuration, and then from the first deployment configuration to a second deployment configuration. The primary and secondary stents are covered by the outer sheath in the pre-deployment configuration. The primary stent is uncovered but the second stent remains covered by the outer sheath in the first deployment configuration. The primary and secondary stents are uncovered by the outer sheath at the second deployment configuration. The primary stent includes a sleeve covering, and the secondary stent is longer than primary stent, and both the primary stent and the secondary stent are self expanding stents.

In another aspect, a method of performing a TIPS procedure includes maneuvering the duet stent deployment system in the pre-deployment configuration to a position at which the primary stent is positioned within a shunt extending between a hepatic vein and a portal vein. The duet stent deployment system is re-configured from the pre-deployment configuration to the first deployment configuration to release the primary stent in the shunt. The duet stent deployment system is then re-positioned to a position at which the distal end of the secondary stent is positioned inside the primary stent, and a proximal end of the secondary stent is positioned at a junction at the hepatic vein to the vena cava. The duet stent deployment system is then reconfigured from the first deployment configuration to the second deployment configuration to release the secondary stent to extend from the junction to the position inside the primary stent.

DETAILED DESCRIPTION

Figure 1:
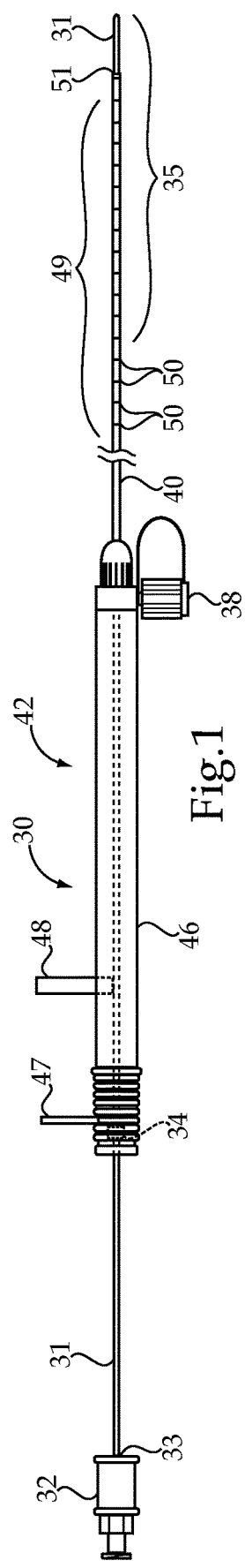
FIG. 1 is a side view of a duet stent deployment system in a pre-deployment configuration.

Hospitals that perform TIPS procedures must normally inventory stent introducers with stents having a variety of lengths to accommodate both physician discretion in deciding a stenting length needed for a particular patient, as well as accommodating the substantial variety in different lengths among patients from a junction of the shunt with the portal vein to a junction of the hepatic vein with the vena cava. Because of the three dimensional structure of these passageways, It can often be time consuming to determine precise stenting length requirements for each individual patient. In many instances, the physician will implant a first sleeve covered stent in the newly made shunt with a first stent deployment device and then reenter with a second stent deployment device to place a second stent to extend from the shunt through the hepatic vein to the junction with the vena cava. While the first stent length is somewhat typical among patients, and being on the order of about four centimeters in length, the length of a second stent, if any is used, can vary substantially among different patients. The second stent being maybe on the order of 5-8 centimeters in length in order to accommodate most patients. The duet stent deployment system of the present disclosure allows for inventorying only a single device that inherently has the flexibility to accommodate the different stenting needs of particular patients, as well as provide the physician with the option of implanting a second stent in an overlapped configuration with the first stent to provide an overall stented length capability for virtually any patient anatomy. Furthermore, the duet stent deployment system can reduce procedure time over prior art TIPS procedures that require entering the patient multiple times with more than one stent deployment system. The duet stent deployment system of this disclosure can also help in reducing guess work in determining an appropriate length for a second implanted stent, if any.

Referring initially to FIGS. 1-4, a duet stent deployment system 30 includes exactly two stents 60 mounted on a distal segment 35 of an inner catheter 31. The two stents 60 include a primary stent 61 and a secondary stent 62. The primary stent 61 includes a sleeve covering 64, which prevents fluid communication between the lumen defined by primary stent 61 and the surrounding tissue. The sleeve covering 64 may be made from PTFE, poly(ether)urethan-eurea or an other biocompatible material. The secondary stent may include a sleeve covering that is identical to that of the primary stent, or may have a different sleeve covering, or no sleeve covering at all. In general, the sleeve covering the primary stent may be non-porous to prevent bile from leaking into the stent and therefore into the blood stream. An inner layer of the sleeve covering may be porous to allow platelets to attach. The secondary stent 62 will always be longer than the primary stent 61, and both the primary stent 61 and the secondary stent 62 are self expanding stents of a type well known in the art. For instance, both primary stent 61 and secondary stent 62 as well as duet stent deployment system 30 may have features similar to currently available ZILVER® available from Cook Incorporated of Bloomington Ind. The length of the primary stent according to this disclosure excludes the length of any anchoring mechanism 63, if any, of the first stent. While primary stent 61 may include an anchoring mechanism 63, secondary stent 62 will not. Thus, the length of the first stent may be determined according to this disclosure by measuring a length of its sleeve.

Figure 2:
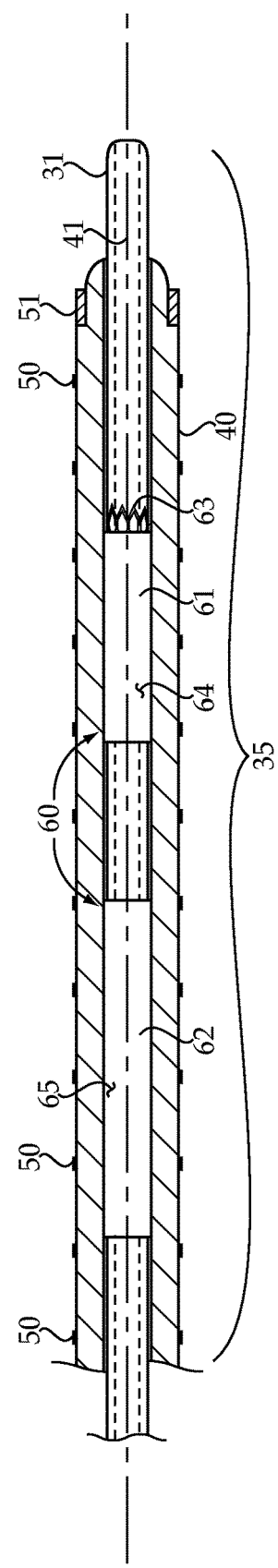
FIG. 2 is an enlarged partially sectioned view of the distal segment of the duet stent deployment system of FIG. 1.
Figure 3:
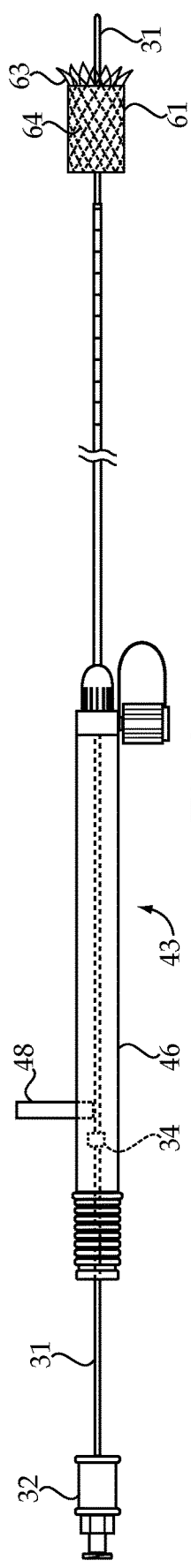
FIG. 3 is a side view of the duet stent deployment system in the first deployment configuration.
Figure 4:
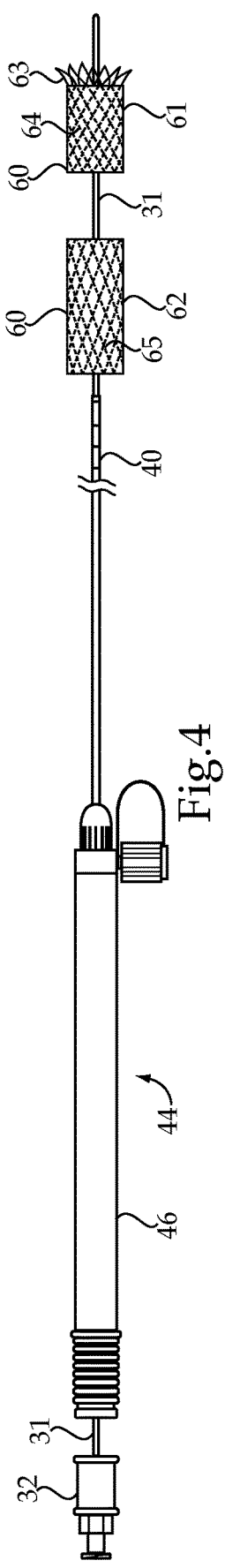
FIG. 4 is a side view of the duet stent deployment system in the second deployment configuration.
Figure 5:
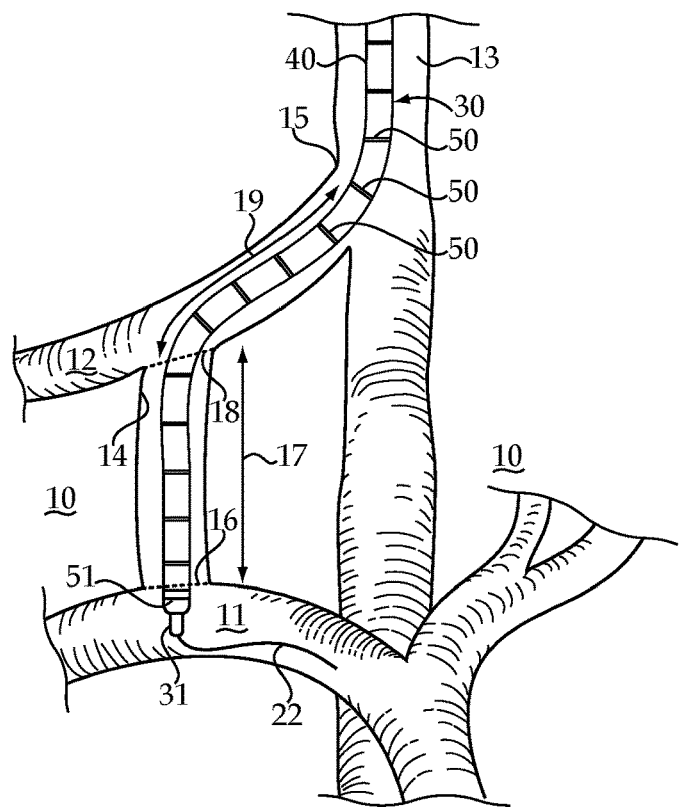
FIG. 5 is a schematic view of a patient's vascular system in the area where a TIPS procedure according to the present disclosure is being performed.

An outer sheath 40 is slidably mounted on the inner catheter 31, and is movable along an axis 41 of the inner catheter 31 from a pre-deployment configuration 42 to a first deployment configuration 43, and then from the first deployment configuration 43 to a second deployment configuration 44. As shown in FIGS. 1 and 2, the primary and secondary stents 61, 62 are both covered by the outer sheath 40 in the pre-deployment configuration 42. As shown in FIG. 3, the primary stent 61 is uncovered but the secondary stent 62 remains covered by the outer sheath 40 in the first deployment configuration 43. As shown in FIG. 4, the primary and secondary stents 61, 62 are both uncovered by the outer sheath 40 at the second deployment configuration 44. Outer sheath 40 may be on the order of 80-125 centimeters in length, and may have an outer diameter on the order of 10 French, but other sizing would also fall within the scope of the present disclosure.

In one specific example, the primary stent 61 may be about four centimeters long, and the secondary stent is less than eight centimeters long, but still longer than the primary stent 61. As used in this disclosure, the term "about" means that the number is rounded to a single significant digit. Thus, both 3.5 centimeters and 4.4 centimeters are about four centimeters according to the present disclosure. As is typical in known stent deployment systems, the duet stent deployment system 30 of the present disclosure may include a radiopaque marker 51 on the distal end of outer sheath 40. In addition, inner catheter 31 may include a lumen sized to receive a wire guide that is used to gain access to the stenting location in a manner well known in the art. Duet stent deployment system 30 may also be similar to typical stent deployment systems by the inclusion of a port 38, which is shown capped, to allow fluids to be injected through the space between the inner catheter 31 and outer sheath 40 in a known manner. Primary stent 61 and secondary stent 62 may have identical expanded outside diameters which are typical for TIPS procedures. For instance, the expanded outside diameters may be 8 or 10 millimeters, but other diameters could be utilized without departing from the intended scope of the present disclosure.

In the duet stent deployment system 30 shown in FIGS. 1-4, a hub 32 is attached to a proximal end 33 of the inner catheter. Outer sheath 40 is connected to a handle 46 that is slidably mounted on the inner catheter 31. While this type of pin and pull actuation may be typical and well known in the art, other actuation structures that allow movement of outer sheath 40 with regard to inner catheter 31 would also fall within the inner intended scope of the present disclosure. For example, one handed devices that utilize a pull connected to the outer sheath that moves responsive to a thumbwheel would also fall within the intended scope of the present disclosure.

Duet stent deployment system 30 may include a first lock 47 that is movable between a locked position in contact with handle 46 as shown in FIG. 1 and an unlocked position detached from handle 46. Duet stent deployment 30 may also include a second lock 48 that is likewise movable between a locked position in contact with handle 46 as shown in FIG. 1 and an unlocked position detached from handle 46. First lock 47 and the second lock 48 may interact with a stop 34 (hidden from view), which may take the form of an enlarged diameter piece attached to inner catheter 31. Lock 47 may inhibit movement of outer sheath 40 with regard to inner catheter 31 such as when duet deployment system 30 is in its pre-deployment configuration 42. Those skilled in the art will appreciate that duet stent deployment system 30 will likely be in its pre-deployment configuration 42 during shipping, storage and while being maneuvered to a treatment site within a patient. In practice, the duet deployment system 30 is locked against movement from the pre-deployment configuration 42 to the first deployment configuration 43 when the first lock 47 is in the locked position as shown in FIG. 1. Likewise, the duet stent deployment system 30 is locked against movement from the first deployment configuration 43 to the second deployment configuration 44 when the second lock 48 is in the locked position as shown in FIG. 3. While locks 47 and 48 may be preferred, they are by no means necessary to the duet deployment system 30. However, by utilizing locks 47 and 48, there may be a lesser likelihood of errors from accidental partial deployment of either primary stent 61 or secondary stent 62 at other than a desirable placement location in the patient. As shown in FIG. 1, both first lock 47 and the second lock 48 are in contact with handle 46 when in their respective locked positions.

Apart from being loaded with exactly two stents 60, duet stent deployment system 30 may also differ from stent deployment systems of the prior art by the inclusion of a ruler measurement segment 49 on one of the outer sheath 40 and inner catheter 41. In the illustrated embodiment, a ruler measurement segment 49 is defined by radiopaque markers 50 that are equally spaced along axis 41. Ruler measurement segment 49 and radiopaque markers 50 may appear similar to features associated with AUROUS® centimeter sizing catheters with a BEACON® tip currently available from Cook Incorporated of Bloomington Indiana. For instance, gold bands spaced one centimeter apart along the ruler segment 49 on the outer surface of outer sheath 40 may be utilized to assist a physician in measuring various key distances within the patient's anatomy. These key distances include distances between different landmarks within the patient. These landmarks include the location where the shunt opens to the portal vein, the junction of the shunt with the hepatic vein, and the distance from that junction to the vena cava. Although longer lengths would still fall within the scope of the present disclosure, the ruler measurement segment 49 may be less than twelve centimeters in length, since the combined length of a primary and secondary stent in even an extremely long deployment applications will still likely be less than ten centimeters. The ruler measurement segment 49 may be especially useful in measuring a distance from the patient's vena cava to a location inside the already deployed primary stent 61 in order to provide at least one centimeter overlap between the two stents 61, 62, while ensuring that the other end of the secondary stent 62 extends all the way to the vena cava in a three dimensional passage that may otherwise be difficult to measure with two dimensional imaging. Although not necessary, the distal end portion of primary stent 62 may include an anchoring mechanism 63 that is outside of sleeve covering 64 and assumes a flared shape when outer sheath 40 is withdrawn sufficiently to reveal anchoring mechanism 63. Nevertheless, primary stent 61 need not necessarily include the optional anchoring mechanism 63.

INDUSTRIAL APPLICABILITY

The present disclosure is generally applicable to any surgical procedure where at least one but no more than two self expanding stents are needed to perform a particular procedure. The disclosure is specifically applicable to procedures in which two stents need to overlap and have a combined length that is constrained by possible uncertain patient anatomy. The present disclosure finds specific applicability to transjugular intrahepatic portosystemic shunting procedures.

Figure 6:
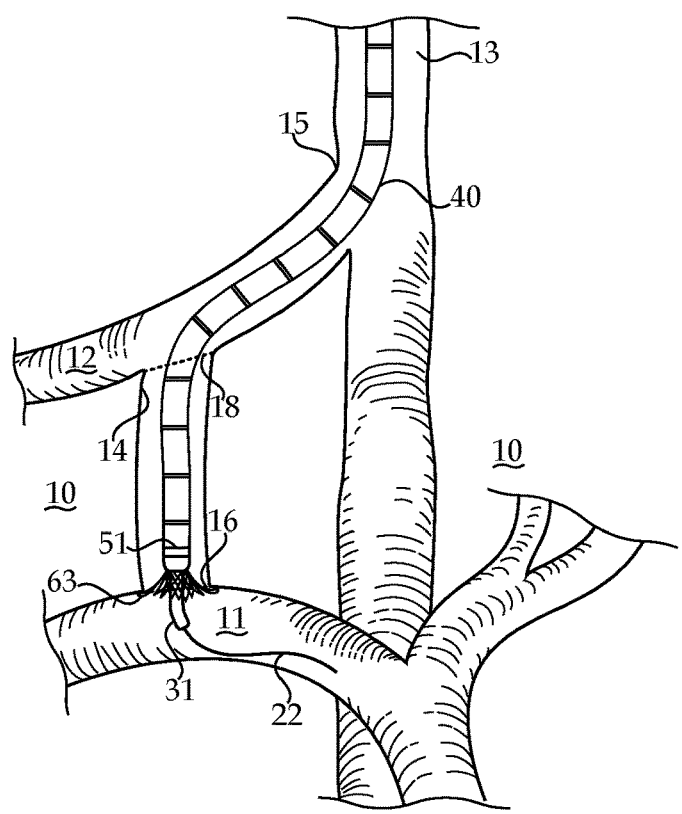
FIG. 6 is a schematic view similar to FIG. 5 after deployment of the primary stent has been initiated.
Figure 7:
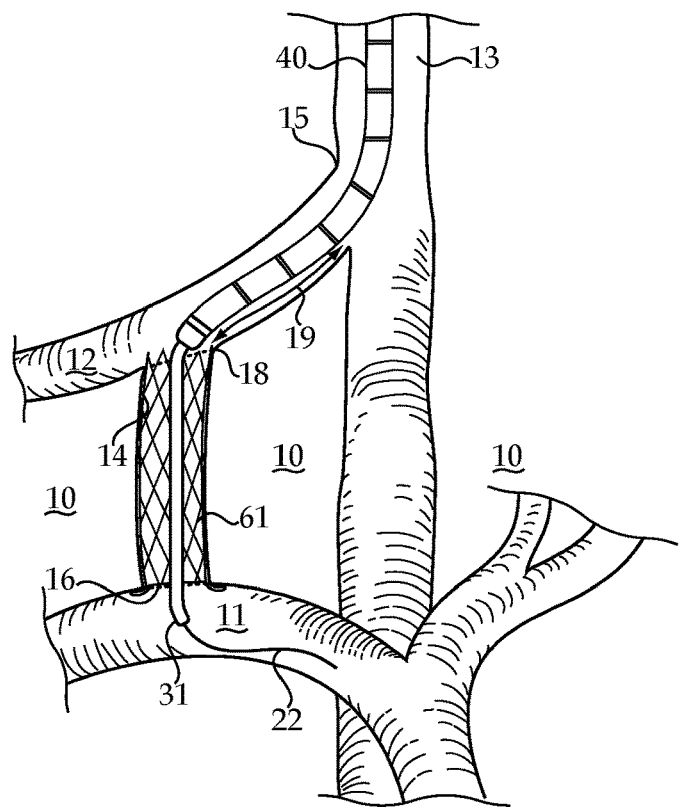
FIG. 7 is a view similar to view FIGS. 5 and 6 after the primary stent has been deployed but before deployment of the secondary stent.
Figure 8:
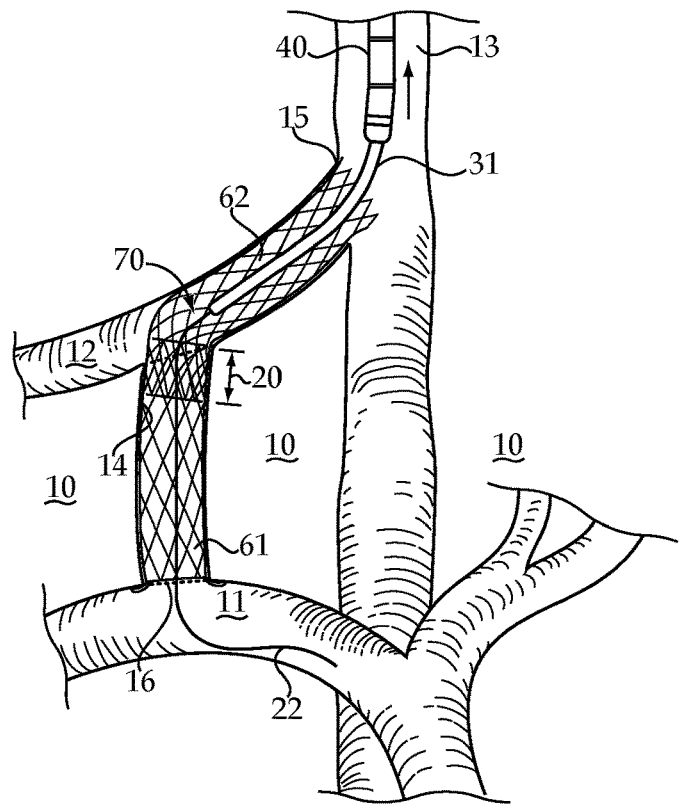
FIG. 8 is a view similar to FIGS. 5-7 except showing the procedure after deployment of the secondary stent with the deployment system being withdrawn upward through the patient's vena cava.

Referring now in addition to FIGS. 5-8 a portion of a TIPS procedure that utilizes the duet stent deployment system 30 of the present disclosure is illustrated. Prior to FIG. 5, the TIPS procedure is typical with the creation of the shunt 14 through liver tissue 10 with an appropriate needle device (not shown). Thereafter, a wire guide 22 extends down through the patients vena cava 13 through a segment of hepatic vein 12, through shunt 14 and into portal vein 11. With the wire guide 22 properly positioned, the duet stent deployment system 30 is advanced over the wire guide 22 into the portal vein 11. In other words, the duet stent deployment system 30 is maneuvered in its pre-deployment configuration 42 to a position at which the primary stent 61 is positioned within shunt 14. Using appropriate imaging, the physician can confirm using radial opaque marker 51, for instance, that the distal end of the duet stent deployment system 30 is properly positioned in the portal vein. This initial maneuvering of duet stent deployment system 30 may be performed with the device 30 in the pre-deployment configuration 42 as shown in FIG. 1. Utilizing the ruler measurement segment 49, while duet stent deployment system 30 remains in the pre-deployment configuration 42, the physician may utilize the radiopaque markers 50 to size the length 17 of shunt 14, which extends from the entrance to shunt 16 at portal vein 11, to the junction 18 where the shunt 14 connects to hepatic vein 12. This information can be useful in confirming that the primary stent 61 is at least as long as the length 17 of shunt 14. Next, the outer sheath 40 may be pulled back a slight distance so that anchoring mechanism 63 is released. Then, the entire duet stent deployment system 30 may be pulled backward until some resistance is felt when anchoring mechanism 63 bears against or contacts the wall of portal vein 11, as best shown in FIG. 6. Deployment of anchoring mechanism 63 may or may not require movement of first lock 47 from its locked position to its unlocked position. However, if first lock 47 has not yet been moved to an unlocked position, after anchoring mechanism 63 is positioned to bear against the wall portal vein 11, the first lock 47 may now be moved from its locked position to its unlocked position. In the event that the primary stent does not include an anchoring mechanism 63, the physician may need to know precisely where the distal end of the primary stent 61 is when concealed by outer sheath 40 in the pre-deployment configuration 42 in order to ensure proper positioning of primary stent 61 when deployed.

The duet stent deployment system 30 is then reconfigured from the pre-deployment configuration 42 as shown in FIG. 1 to the first deployment configuration of 43 as shown in FIG. 3 to release the primary stent 61 in shunt 14. When this occurs, the outer sheath 40 is slid with respect to inner catheter 31 to the first deployment configuration 43 to release primary stent 61 to occupy shunt 14. After releasing the primary stent 61, its positioning may be confirmed through appropriate imaging. Thereafter, the duet stent deployment system 30 is repositioned to prepare for deployment of the secondary stent 62. At this point, the physician may use the ruler measurement segment 49 on outer sheath 40 to take a second measurement in order to assess where to place the secondary stent 62. For instance, the physician may desire one end of secondary stent 61 to the to be located at the junction 15 of hepatic vein 12 to vena cava 13, and the opposite end of the secondary stent 61 to be positioned inside, in an overlapping relationship with primary stent 61. Uncertainty arises in accurately determining the distance 19 from the patient's vena cava to the junction of shunt 14 with the hepatic vein 12. The secondary stent should be long enough to accommodate measurement distance 19 plus an overlap distance 20. To be clear, the primary stent 61 overlaps secondary stent 62. This overlap may occupy this distance as shown as measurement 20 in FIG. 8. It may be desirable that a minimum overlap of one centimeter be achieved. However, a greater overlap, a lesser overlap or no overlap at all would also fall within the intended scope of the present disclosure. In order to inhibit bile from entering the bloodstream, no portion of the tissue wall that defines shunt 14 should be left uncovered.

After the measurement distance 19 is noted using the radiopaque markers of ruler measurement segment 49, the duet stent deployment system 30 can be properly positioned with the help of radiopaque marker 51, and knowing where secondary stent 62 is positioned on inner catheter 31 with respect to radiopaque marker 51. Thus, the duet stent deployment system 30 may be repositioned to a position at which the distal end of the secondary stent 62 is positioned inside the primary stent 61, and a proximal end of this secondary stent 62 is positioned at junction 15 of the hepatic vein to the vena cava 13. The secondary stent 62 can now be readied for release. If included, the second lock 48 can be moved from its locked position to its unlocked position, by removing the pin from the system 30, and the outer sheath 40 slid with respect to inner catheter 31 to release and implant the secondary stent 62. In other words, the duet stent deployment system 30 is reconfigured from the first deployment configuration 43 as shown in FIG. 3 to the second deployment configuration 44 as shown in FIG. 4 to release the secondary stent 62 to extend from the junction to the vena cava to a position inside primary stent 61. Thereafter, the duet stent deployment system 30 can be withdrawn from the patient leaving wire guide 22 in place. If deemed necessary, a balloon catheter (not shown) can be maneuvered along wire guide 22 and inflated within both the primary stent 61 and the secondary stent 62, especially at the main junctions 16, 18 and 15 to ensure patency of the stents. When completed, the combined primary stent and secondary stent 70 may have an overlapping configuration and extend from the entrance 16 to shunt 14 all the way to junction 15 where hepatic vein 12 connects to vena cava 13.

Those skilled in the art will appreciate that if first and second locks 47 and 48 are included, the first lock is maintained in its locked position and the second lock 48 is maintained in its locked position while the duet stent deployment system 30 is being maneuvered in the predeployment configuration 42. Likewise, the second lock 48 may be maintained in its locked position during the step of reconfiguring the duet stent deployment system 30 from the predeployment configuration 42 to the first deployment configuration 43. In addition, the second lock 48 may be maintained in its locked position while the duet stent deployment system 30 is being repositioned prior to deployment of the secondary stent 62. Finally, the second lock 48 may be moved to its unlocked position to enable movement of the duet stent deployment system 30 from the first deployment configuration 43 to the second deployment configuration 44. Unlike prior art TIPS procedures, both the primary stent 61 and the secondary stent 62 are both deployed prior to withdrawal of the inner catheter 31 from the patient.

By utilizing exactly two stents 60 on a single delivery system 30, the physician is allowed great flexibility on the fly during the TIPS procedure. In addition, loading of the two stents 60 on the single introducer 30 allows for fewer interventions and a single access into the patient, thus saving time and reducing patient risks during the TIPS procedure. If utilized, the dual safety lock strategy (first and second locks 47 and 48) may be provided in order to prevent accidental deployment of the secondary stent 62 before adjustment has been made after the primary stent 61 has been deployed. This single access technique may reduce costs verses delivering two separate stents with two separate delivery catheters. The TIPS procedure time is also reduced with requirement of only a single access. Furthermore, hospitals may need to only inventory a small number of duet stent deployment systems 30 to accommodate the wide variety of potential patients, verses inventorying multiple stent deployment systems each loaded with stents of different lengths in order to accommodate the needs of particular patients. One important aspect of the TIPS procedure to note is that some physicians place a second stent if the first stent is not long enough to extend from the portal vein 11 to the vena cava 13. This can be a burden because the physician may have to use an expensive stent with anchoring features, which should be unnecessary, and may be problematic for the secondary stent 62. Thus, duet stent stent deployment system 30 may include exactly one stent with an anchoring mechanism 63. If included, the anchoring mechanism 63 may have a structure similar to the anchor feature appearing in stents available from Cook Incorporated of Bloomington Ind.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of performing a transjugular intrahepatic shunting procedure with duet stent deployment system that includes exactly two stents mounted on a distal segment of an inner catheter, and the two stents include a primary stent and a secondary stent; an outer sheath slidably mounted on the inner catheter, and being movable along an axis of the inner catheter from a predeployment configuration to a first deployment configuration, and then from the first deployment configuration to a second deployment configuration; and the primary stent includes a sleeve covering, and the secondary stent is longer than the primary stent, and both the primary stent and the secondary stent are self-expanding stents, and the method comprising the steps of:
   maneuvering the duet stent deployment system in the predeployment configuration to a position at which the primary stent is positioned within a shunt extending between a hepatic vein and a portal vein;
   reconfiguring the duet stent deployment system from the predeployment configuration to the first deployment configuration to release the primary stent in the shunt;
   repositioning the duet deployment system to a position at which a distal end of the secondary stent is positioned inside the primary stent, and a proximal end of the secondary stent is positioned at a junction of the hepatic vein to the a vena cava; and
   reconfiguring the duet stent deployment system from the first deployment configuration to the second deployment configuration to release the secondary stent to extend from the junction to a position inside the primary stent.

2. The method of claim 1 including a step of measuring a distance from the junction to the shunt using a ruler measurement segment of the outer sheath, which is defined by radiopaque markers equally spaced along the axis, prior to the step of reconfiguring the duet stent deployment system from the first deployment configuration to the second deployment configuration.

3. The method of claim 1 wherein the step of reconfiguring the duet stent deployment system from the first deployment configuration to the second deployment configuration includes implanting the secondary stent to a position at which the primary stent overlaps the secondary stent over a distance greater than about one centimeter.

4. The method of claim 1 including a step of measuring a length along the axis of the shunt using a ruler measurement segment of the outer sheath, which is defined by radiopaque markers equally spaced along the axis, prior to the step of reconfiguring the duet stent deployment system from the predeployment configuration to the first deployment configuration.

5. The method of claim 1 including a step maintaining a first lock in a locked position and a second lock in a locked position during the maneuvering step;
   moving the first lock from the locked position to an unlocked position to enable movement of the duet stent deployment system from the predeployment configuration to the first deployment configuration;
   maintaining the second lock in the locked position during the step of reconfiguring the duet stent deployment system from the predeployment configuration to the first deployment configuration;
   maintaining the second lock in the locked position during the step of repositioning the duet stent deployment system; and
   moving the second lock from the locked position to an unlocked position to enable movement of the duet stent deployment system from the first deployment configuration to the second deployment configuration.

6. The method of claim 1 wherein the combined primary stent and the secondary stent extend from the portal vein to the junction with the primary stent overlapping the secondary stent over a distance greater than about one centimeter.

7. The method of claim 1 including the steps of:
   deploying an anchoring mechanism; and
   withdrawing the duet stent deployment system until the anchoring mechanism contacts the portal vein at an entrance to the shunt.

8. The method of claim 1 wherein the primary stent and the secondary stent are released prior to withdrawing the inner catheter and the outer sheath out through the vena cava.

9. The method of claim 8 wherein the combined primary stent and the secondary stent extend from the portal vein to the junction with the primary stent overlapping the secondary stent over a distance greater than about one centimeter.

10. The method of claim 9 including a step of measuring a distance along the axis from the junction to the shunt using a ruler measurement segment of the outer sheath, which is defined by radiopaque markers equally spaced along the axis, prior to the step of reconfiguring the duet stent deployment system from the first deployment configuration to the second deployment configuration;
   wherein the step of reconfiguring the duet stent deployment system from the first deployment configuration to the second deployment configuration includes implanting the secondary stent to a position at which the primary stent overlaps the secondary stent over a distance greater than about one centimeter;
   measuring a length along the axis of the shunt using a ruler measurement segment of the outer sheath, which is defined by radiopaque markers equally spaced along the axis, prior to the step of reconfiguring the duet stent deployment system from the predeployment configuration to the first deployment configuration;
   maintaining a first lock in a locked position and a second lock in a locked position during the maneuvering step;
   moving the first lock from the locked position to an unlocked position to enable movement of the duet stent deployment system from the predeployment configuration to the first deployment configuration;
   maintaining the second lock in the locked position during the step of reconfiguring the duet stent deployment system from the predeployment configuration to the first deployment configuration;
   maintaining the second lock in the locked position during the step of repositioning the duet stent deployment system; and
   moving the second lock from the locked position to an unlocked position to enable movement of the duet stent deployment system from the first deployment configuration to the second deployment configuration.

* * * * *